() United States Patent  
König et al.

(10) Patent No.: US 11,403,793 B2  
(45) Date of Patent: Aug. 2, 2022

(54) X-RAY SYSTEM FOR THE ITERATIVE DETERMINATION OF AN OPTIMAL COORDINATE TRANSFORMATION BETWEEN OVERLAPPING VOLUMES THAT HAVE BEEN RECONSTRUCTED FROM VOLUME DATA SETS OF DISCRETELY SCANNED OBJECT AREAS

(71) Applicant: Ziehm Imaging GmbH, Nuremberg (DE)

(72) Inventors: Thomas König, Nuremberg (DE); Klaus Hörndler, Nuremberg (DE)

(73) Assignee: Ziehm Imaging GmbH, Nuremberg (DE)

( * ) Notice: Subject to any disclaimer, the term of this patent is extended or adjusted under 35 U.S.C. 154(b) by 216 days.

(21) Appl. No.: 16/825,830

(22) Filed: Mar. 20, 2020

(65) Prior Publication Data

US 2020/0302660 A1 Sep. 24, 2020

(30) Foreign Application Priority Data

Mar. 21, 2019 (DE) .......................... 102019001988.1

(51) Int. Cl.
*G06K 9/00* (2022.01)
*G06T 11/00* (2006.01)
(Continued)

(52) U.S. Cl.
CPC ............ *G06T 11/006* (2013.01); *A61B 6/032* (2013.01); *A61B 6/0487* (2020.08);
(Continued)

(58) Field of Classification Search
CPC ..... A61B 6/032; A61B 6/4085; A61B 6/5205; A61B 6/5241; A61B 6/4441;
(Continued)

(56) References Cited

U.S. PATENT DOCUMENTS 8,805,037 B2 * 8/2014 Pack ..................... G06T 11/006  
382/128  
2009/0018435 A1 * 1/2009 Hsieh ................... A61B 6/5288  
600/425

(Continued)

FOREIGN PATENT DOCUMENTS

DE 10 2012 104 599 12/2012

OTHER PUBLICATIONS

Examination Report, Application No. 10 2019 001 998.1, dated Feb. 3, 2020.

*Primary Examiner* — Shervin K Nakhjavan
(74) *Attorney, Agent, or Firm* — Knobbe Martens Olson & Bear, LLP (57) ABSTRACT

This disclosure relates to an X-ray system for obtaining referencing information in the form of a coordinate transformation between a first volume and a second volume, with the volumes partially overlapping. In this case two partially overlapping subareas of an extended object having a continuous distribution of a physical size are discretely sampled with a measuring apparatus; the volumes are reconstructed and the overlapping volumes are iteratively changed, wherein a bandpass filter is applied to the overlapping volumes, where said bandpass filter changes the Fourier domain representation of the overlapping volumes. The filtered overlapping volumes, in which the artifacts, induced by the discrete sampling, are matched, are compared by means of a measure of similarity, which is iteratively maximized by means of mathematical optimization. The coordinate transformation with the maximum result for the measure of similarity is used as the optimal coordinate transformation for combining the two volumes in the correct position. One application is the combination of 3D X-ray volumes that have been reconstructed by means of a cone (Continued)

beam computed tomography scanner, preferably a 3D C-arm.

24 Claims, 3 Drawing Sheets

(51) Int. Cl.
    *A61B 6/00*     (2006.01)
    *A61B 6/03*     (2006.01)
    *G06T 7/262*     (2017.01)
    *G06T 7/00*     (2017.01)
    *G06T 7/35*     (2017.01)
    *A61B 6/04*     (2006.01)

(52) U.S. Cl.
    CPC .......... *A61B 6/4085* (2013.01); *A61B 6/4405* (2013.01); *A61B 6/4441* (2013.01); *G06T 7/0012* (2013.01); *G06T 7/262* (2017.01); *G06T 7/35* (2017.01); *A61B 2562/02* (2013.01); *G06T 2207/20024* (2013.01); *G06T 2207/20056* (2013.01); *G06T 2207/30004* (2013.01); *G06T 2211/424* (2013.01)

(58) Field of Classification Search
CPC ....... A61B 6/4405; A61B 6/03; A61B 6/0407; A61B 6/469; A61B 6/5258; A61B 2090/376; A61B 6/4258; A61B 1/00186; A61B 2090/3762; A61B 2090/3764; G06T 2207/10081; G06T 11/005; G06T 11/008; G06T 2211/424; G06T 2207/30004; G06T 7/0012; G06T 2210/41; G06T 15/08; G06T 2207/20024; G06T 2207/30168; G06T 2211/40; G06T 7/262

See application file for complete search history.

(56) References Cited

U.S. PATENT DOCUMENTS

| | | | | |
|---|---|---|---|---|
| 2011/0075905 | A1* | 3/2011 | Noshi | A61B 6/032 382/131 |
| 2012/0294501 | A1* | 11/2012 | Kyriakou | A61B 6/5258 382/131 |
| 2014/0253544 | A1* | 9/2014 | Arakita | G06T 7/0012 345/419 |
| 2016/0171724 | A1* | 6/2016 | Nett | G06T 11/006 382/131 |

* cited by examiner

X-RAY SYSTEM FOR THE ITERATIVE DETERMINATION OF AN OPTIMAL COORDINATE TRANSFORMATION BETWEEN OVERLAPPING VOLUMES THAT HAVE BEEN RECONSTRUCTED FROM VOLUME DATA SETS OF DISCRETELY SCANNED OBJECT AREAS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to X-ray imaging systems and methods for determining a coordinate transformation between overlapping reconstructed volumes.

Description of the Related Art

Methods for obtaining volumes that are formed by combining the individual volumes are known from the prior art.

A method for minimizing cone beam artifacts by supplementing missing frequencies in the Fourier domain is known from the document DE10014668A1.

The document DE102007025862A1 discloses a system and a method for the geometry-based registration of partial volumes and for forming a composite volume with the objective of avoiding artifacts.

The document DE102007034218B4 discloses an apparatus and a method for combining an image, consisting of at least two individual images, an object provided with markers, wherein optical images are used for registration.

The document DE102008062030A1 discloses an arrangement and a method for positioning objects to be imaged and for 3D stitching, wherein a joint control of the C-arm and the patient couch is provided using position sensors.

The document EP520778B1 discloses a method for tomographic imaging by means of oblique rays, so that artifacts, which are caused by stitching two scan data sets, are eliminated, and wherein the plane of a scan is not perpendicular to the Z axis.

It is known from the document by Seungeon Kim, Yongjin Chang, and Jong Beom Ra: "Reduction of Cone Angle Effect in Cardiac Motion Correction Based on Partial Angle Reconstructed Images in CT", 4th International Conference on Image Formation in X-Ray Computed Tomography, Bamberg, Germany, Jul. 18 to 22, 2016, Proceedings of the 4th CT Meeting, page 439 ff., to adjust cone beam artifacts for motion compensation in cardiac CT.

The document US20140267267A1 discloses a device and a method for 3D stitching of overlapping individual volumes, wherein the voxel values in the overlapping volumes are used for stitching.

The document US20150371420A1 discloses a method for registering partial volumes and for combining the partial volumes to form a composite volume using artifact positions in the X-ray volume.

The document U.S. Pat. No. 6,711,293B1 discloses a method for combining partial volumes, in which method extreme pixel values of subtraction images are used for registration.

The document U.S. Pat. No. 9,129,389B2 discloses a CT apparatus and a method, in which the contrast differences between CT slice volumes, recorded one after the other over time, are corrected.

The document WO11039672A1 discloses a method for 3D stitching of partial volumes, in which image data of the individual volumes are used for registration.

The document WO12048070A1A discloses a method for 3D stitching of overlapping partial volumes, wherein an alpha-blending/morphing method is provided in the overlapping volumes; and the voxels in the individual volumes are weighted before stitching, where the weighting depends on the distance of the voxel from the edge of the individual volume.

The document WO12139031A discloses a method for generating a composite volume by means of cone beam CT, in which method cone beam artifacts are used as a measure of an inaccurate volume stitching.

The document WO16097174A1 discloses a method for 3D stitching using the isocenter positions of the individual volumes. There is a need for a method for obtaining an improved volume that is made up of the recordings of images, the Fourier domains of which are incompletely sampled. Furthermore, there is a need for an improved method for markerless registration of, in particular, low-contrast computed tomography images to form a 3D composite volume as well as for a diagnostic X-ray system for carrying out the method.

SUMMARY

One object of embodiments of the present disclosure is to create a method that provides an algorithm for determining a coordinate transformation, with which, for example, a second of two overlapping volumes is registered with respect to a first volume and with which a second volume is added to a first volume in the correct position, so that the disadvantages of known methods in the case of incompletely sampled Fourier domains are eliminated; and the accuracy of the registration of the individual volumes is increased. Furthermore, it is an object of the present technology to create a diagnostic X-ray system consisting of a controllable cone beam computed tomography scanner and a controllable support structure, which is motor adjustable, in order to implement the method.

Said objects are achieved by means of the features disclosed in the independent claims. Other, particularly advantageous embodiments and further developments shall become apparent from the dependent claims.

With regard to the method the objects are achieved in accordance with the present technology by means of the features disclosed in claim 1.

Advantageously, a coordinate transformation is determined iteratively in the course of the registration, starting from an initial, estimated coordinate transformation, wherein the degree of congruence between the modified or, more specifically, the filtered voxel values of the first and the second overlapping volume reaches a maximum value.

One advantage of the present technology is to generate larger scan volumes, for example, especially along the long axis of the support structure, for example, along the spine or a lower extremity of a patient. For example, it is easier to display scoliosis and its correction in this way during surgical intervention.

The present technology for registering and for combining individual volumes into a composite volume is implemented preferably in software. A largely software-based implementation has the advantage that even methods that have already been used in the past for volume reconstruction and for combining the individual volumes into a composite volume for image recording systems can be easily upgraded by means of a software update, in order to work in the manner in accordance with the present technology. In this respect said object is also achieved by means of a corresponding computer program product with a computer program, which can be loaded directly into a memory device of an image recording system, for example, a cone beam computed tomography scanner, with program sections, in order to carry out all of the steps of the method of the present technology, when the computer program is executed in the control apparatus. In addition to the computer program, such a computer program product can include, if necessary, additional components, such as, for example, documentation and/or additional components, including hardware components for using the software.

In order to transport to the control apparatus and/or for storage on or in the control apparatus, a computer-readable medium, for example, a memory stick, a hard disk or some other portable or permanently installed data carrier, can be used, on which those program sections of the computer program that can be read and executed by a computer unit of the control apparatus are stored. The transport may also be facilitated by a connection to a hospital information system, which is connected to a network, to a radiology information system or to a global network, in which systems the program sections of the computer program that can be read and executed by a computer unit of the control apparatus are stored. For this purpose the computer unit can have, for example, one or more interacting microprocessors or the like.

Objects of the present technology are achieved, in particular, by the feature that two overlapping volumes of an object area are recorded together with estimated registration information in the form of a coordinate transformation; and, starting from the initial estimated coordinate transformation, an iterative change in the coordinate transformation is used to calculate the resulting overlapping volumes, which are filtered by an algorithm, which adjusts the artifacts in the overlapping volumes and which contains a bandpass filter, which a.) transforms the overlapping volumes into the Fourier domain, removes in the Fourier domains all frequencies, which do not occur in the Fourier representation of the respective other overlapping volume, from the respective Fourier domains, for example, by multiplication by 0, and, thus, produces two filtered Fourier domains of the overlapping volumes, or b) acts on the overlapping volumes in the spatial domain, which in its effect also removes all frequencies, which do not occur in the corresponding Fourier domains of the respective other overlapping volume, from the respective corresponding Fourier domains and, thus, produces two filtered versions of the overlapping volumes, wherein a measure of similarity of the filtered overlapping volumes is determined, and wherein the coordinate transformation, which generates the optimal measure of similarity of the filtered overlapping volumes, is used as the optimal coordinate transformation for registration. In this case the frequencies that are not recorded can be identified directly in the Fourier domain by the fact that the absolute amount, present therein, is less than a threshold value to be selected. As an alternative, in the presence of corresponding information the unscanned areas can be calculated from the knowledge of the recording geometry or, more specifically, the scanning mode/scanning trajectory and the special design of a measuring method.

As a result, the overlapping volumes of the two individual volumes are each subjected to filtering in order to adjust the artifacts, said artifacts corresponding in the context of the present technology to an incompletely sampled Fourier domain of at least one subarea in at least one partial volume. For example, in the case of the computed tomography said artifacts may originate from the group of cone beam artifacts; or such artifacts may originate from an incomplete angular coverage (scan angle range less than, for example, 180 degrees plus cone angle).

The result of the iterative method with the estimated coordinate transformation for the first iteration step is a comparatively improved coordinate transformation, which is used for referencing the individual volumes in the spatial domain. The individual volumes are shifted and rotated relative to each other with the determined optimal coordinate transformation (inelastic registration, i.e., globally valid coordinate transformation), or additionally deformed (elastic registration, i.e., local or, more specially, voxel-by-voxel coordinate transformation), wherein, for example, a first recorded volume data set is connected to an intrinsic coordinate system, and the second or all other volume data sets relating to the intrinsic coordinate system are registered. After registration of the two volumes, the voxel values of the overlapping areas are merged by methods known from the prior art, in order to avoid the generation of artifacts at the transitions between the two volumes. In so doing, the central or remaining volumes outside the overlapping volumes remain unchanged in the absorption values of the voxels, with the exception of the effects of interpolation steps that are necessary in order to be able to map both volumes to the same discrete grid. However, when the individual volumes are merged, redundant image information in the overlapping area is used in such a way that the highest possible image quality of the reconstructed composite volume is achieved, in order, for example, to use the radiation dose that is employed in an optimal way.

As a result, the algorithms of the present technology for evaluating the overlapping areas of a first and a second volume has to determine the relative position and orientation of the two volumes relative to one another. In this case the algorithm uses information about an assumed or estimated relative position and orientation of the individual volumes. These assumed values for the position and orientation of the individual volumes are obtained, for example, from the traversing path and the traversing direction of the cone beam computed tomography scanner, preferably a C-arm X-ray device, or the support structure of the object, for example, a patient couch, in the room.

Furthermore, it is provided in the context of the present technology to use the determined optimal registration information, in order to produce a registration between the cone beam computed tomography scanner, preferably a C-arm, and the coordinate system of the support structure. Such a registration enables navigation in the volume composed of the individual volumes.

In order to produce a registration or referencing between the coordinate system of a cone beam computed tomography scanner and the coordinate system of the support structure, an extended phantom with X-ray positive structures can be used preferably as the object, instead of a patient; and the registration step can take place in terms of time before an X-ray examination. If the support structure and the cone beam computed tomography scanner are referenced with respect to one another, then this referencing remains valid until the cone beam computed tomography scanner and/or the support structure of the object are moved in a non-reproducible manner. As long as the registration is valid, the support structure can be moved, for example, into a well-defined position in the coordinate system of the cone beam computed tomography scanner.

It is also provided in the context of the present technology that the reference coordinate system may be determined not by the first volume V1, but rather by the second volume V2. As an alternative, it is provided to use a third, for example, external or spatially fixed coordinate system, to which the two volumes V1 and V2 are mapped accordingly. In this case the steps, listed above, change as appropriate.

The combination of the two individual volumes V1 and V2 takes place in the spatial domain, using the coordinate transformation T12 (i) associated with the optimal measure of similarity S (i).

In order to avoid artifacts in the spatial domain, it is provided to determine the contributions of the respective individual volumes at the transitions between the overlapping areas, present in both volumes V1 and V2, and areas, which are present only in an individual volume V1 or V2, taking into account a transition function that avoids hard transitions; for example, by means of a sigmoid, instead of a rectangle.

It is optionally provided to increase the sub-pixel accuracy by means of interpolation, i.e., by scaling up the volumes, then registering and then scaling down the image resolution.

In order to generate a composite volume composed of two individual volumes, it may be necessary to suitably combine those image regions that are present in both individual volumes. It is provided to arithmetically average the original gray values of the voxels, as a result of which the cone beam artifacts are retained.

Therefore, it may be advantageous to use in each case the voxel from the individual volume that has fewer cone beam artifacts. Furthermore, it is also provided to average the voxels from both volumes in a weighted manner, the weighting factors being determined from the respective artifact level, for example, in accordance with the cone beam angle, assigned to a voxel, or a cone angle, averaged over the scan range, in the case of a non-circular focus trajectory of a scan. Furthermore, it is provided to determine the weighting factors by means of the measurement error of the discrete sampling at a voxel. For example, the recording situation can have the result that one of the two partial volumes has a higher noise level in subareas, so that, when combined, a corresponding voxel is given a weaker weighting.

Furthermore, it is also provided in the context of the present technology that after the registration, but before the combination of the partial volumes, the missing areas or, more specifically, the frequencies in one of the Fourier domains are then filled with the corresponding areas or, more specifically, frequencies from the respective other Fourier domain for each overlapping volume, if and in so far as they are present there, in order to attenuate the artifacts in the composite volume to be combined in the best possible way.

In the event of a slight movement-related displacement of parts of an object between the individual recordings of the scans of the 3D data sets, it is provided in the context of the present technology to perform an elastic registration, in addition to a rigid registration of the two volumes.

It is provided to use the obtained registration information for a calibration between the cone beam computed tomography scanner and the support structure. In this case the calibration/registration remains valid as long as the shifts of the cone beam computed tomography scanner and/or the support structure can be reproduced. The obtained calibration data can also be used, for example, to avoid collisions.

It is provided to adjust the cone beam computed tomography scanner, in particular, a mobile C-arm, by adjusting a so-called wigwag angle about a pivot axis that is perpendicular in space and contains the scan plane of the first scan. In this case the angular orientation of the recording unit is changed in the case of a stationary mobile tripod. This is done by means of a motorized drive or manually by the user, for example, with the aid of a reference marking, or a display of a position sensor reading of this angle.

If the area of measurement is changed in this way, then this change corresponds to a rotation, instead of a translation of the recording unit. In order to be able to shift the center of the area of measurement, for example, back again to the spine, it is possible to use a linear axis, which is present at the cone beam computed tomography scanner, in particular, at a C-arm. This aspect may include a traversing path that is also available on the linear axis, since said linear axis may also be needed during the recording, in order to maintain a virtual isocenter.

A change in the orientation of the recording unit can aggravate collision situations. Therefore, in this case it is particularly important to conduct additional collision tests. As above, such collision tests should be conducted, if possible, completely before the start of the first scan, and especially if there is a corresponding motorization of the deflection, in order to shorten, for example, the time during which a patient holds his/her breath.

It is provided that a user triggers the individual steps manually through an input interface, for example, by pressing a button or an input surface on a touch screen/GUI.

It is provided that the entire cone beam computed tomography scanner is moved in a motor-controlled manner, for example, in the case of a ceiling mounted cone beam computed tomography scanner, in particular, a C-arm.

In the case of a mobile chassis, it is provided that the user brings the wheels into a 90 degree position before the start of a scan, or that the cone beam computed tomography scanner does this automatically. This is preferably verified by the device software by means of a position sensor for the alignment of the wheels. At the same time the user ensures that there is a sufficient traversing path available for all positions. The initial position of the cone beam computed tomography scanner has to be selected in such a way that all other positions can be reached. Then the display of the C-arm gives instructions on how far the C-arm and, if necessary, in which direction it should be moved. For example, for an individual volume size of 16 cm and an overlap of 2 cm, a movement of 14 cm would be requested.

In the case of a motorization of the mobile chassis, the cone beam computed tomography scanner can carry out the required movement itself preferably with the aid an existing position sensor. This motorized movement is carried out preferably only if the user touches, for example, a button or an area on a touch screen/GUI, in order to be able to abort the process immediately in the event of an impending collision.

The methods of the present technology are different from the known methods due to the fact that for the iterative determination of the coordinate transformation in the manner described above, the overlapping areas, assumed to be different within each iteration step, are filtered in such a way that only the areas that are present in both Fourier domains of the two partial volumes are used to determine the measure of similarity.

A similarity operator is then applied to the two filtered overlapping volumes in the spatial domain or in the Fourier domain by iteratively changing the coordinate transformation and determining a measure of similarity S (i) for each iteration step i. The coordinate transformation, in which the value of S (i) is optimal, is used as the optimal coordinate transformation for registering the volumes V1 and V2.

It is expedient to store the determined coordinate transformation as referencing information between the cone beam computed tomography scanner and the object support structure. The storage of the coordinate transformation or, more specifically, the referencing information can be used in this embodiment to combine the partial volumes to be recorded in the future directly without re-optimization.

In the event that a cone beam computed tomography scanner, for example, a C-arm, is used, the relative change in the position and/or the relative change in the orientation of the cone beam computed tomography scanner with respect to the ROI is and/or are optionally carried out by a manual and/or motor-controlled displacement of the cone beam computed tomography scanner and/or the support structure, preferably a patient couch, with the object under examination. The change in the position and/or orientation between the recording of the first 3D data set and the recording of the second 3D data set takes place in such a way that there is a necessary overlap of the partial volumes.

DETAILED DESCRIPTION OF THE PREFERRED EMBODIMENT

Known image recording devices for imaging or measuring objects are always limited to one area of measurement or to one image field, within which they scan and optionally display an object, due to the measuring method that is used. Outside such an area of measurement there is by definition no information about the object. If the area of measurement is too small for a selected application, then it is known to expand it by taking several images. In this case the composite of these areas of measurement depicts the object preferably in such a way that the edges of said areas of measurement are at least adjacent to one another, generally even overlap. It is known that an error-free and artifact-free combination of individual areas of measurement to form an entire area of measurement is made possible by precise knowledge of the geometries and measuring methods of the image recording devices by determining the coordinate transformations between the areas of measurement. Furthermore, it is known that, in the absence of such knowledge, the coordinate transformations can be obtained from the comparison of corresponding image areas in the overlapping areas of the individual areas of measurement. In this case an initially assumed coordinate transformation is improved preferably in an iterative optimization process until the process has achieved sufficient congruence of the two areas of measurement in their overlapping area in accordance with an abort criterion. The degree of congruence is described by means of a quantitatively formulated measure of similarity or dissimilarity, which is maximized or minimized accordingly, i.e., optimized, by the optimization process. Such methods are known, in particular, as an inelastic or elastic registration. Since it is possible at any time to transform a measure of similarity to be maximized into a measure of dissimilarity to be minimized, for example, by multiplication by "4", the term measure of similarity is used below to represent both optimization strategies.

In the general case the areas of measurement correspond to the volume data sets of a spatial area that has a continuum of physical values that is discretely and possibly incompletely sampled within the volume with the measuring apparatus, the volume being described, for example, by means of voxels at periodic grid points. In this case the space can, but does not have to, correspond to a physical space and, therefore, can have one, two, three, or more dimensions. As a result, corresponding volumes of higher dimensions can be characterized, for example, by three spatial dimensions plus a time coordinate (4D) or, for example, by three spatial dimensions that are recorded in several spectral ranges.

The volume can be sampled directly or calculated from intermediate steps that have been recorded. The latter is used, for example, in X-ray computed tomography, where a three dimensional representation of the absorption properties of the object under examination, for example, a patient, is calculated from the recording of two dimensional X-ray projections, for example, by means of the method of a filtered back projection.

Sampled volumes always have a representation in the Fourier domain that can generally be calculated by a discrete Fourier transformation. However, there is a one-to-one correspondence between the representations in the spatial domain and in the Fourier domain even without an explicit calculation thereof. In particular, measurement errors or, more specifically, artifacts that manifest themselves in the recorded volume, the so-called spatial domain, may be due to a direct correspondence in the Fourier domain without having to directly calculate the Fourier transformation. In this case the coordinate axes in the Fourier domain are represented by the wave numbers or, more specifically, the frequencies along the corresponding spatial axes, and, thus, a coordinate in the Fourier domain corresponds to a tuple of wave numbers or frequencies along these axes (hereinafter referred to as frequencies). In general, there is a complex number, which contains the amplitude and phase of a (spatial) frequency, at such a Fourier coordinate. If the corresponding frequency was not recorded by the measuring method, then this number is ideally zero at the corresponding coordinate in the Fourier domain. However, owing to a limited numerical precision or a downstream image processing, the complex number that is actually present may be different from zero, but generally has a comparatively small absolute value. In this case it is described below as a "missing" or "not sampled", "not available" or "not recorded" frequency. Similarly, the "removal" of frequencies shall be mentioned, if the complex numbers, recorded there, are set to zero or alternatively a very small number.

It is known that scanning can result in artifacts during the reconstruction of the resulting volume. One class of such artifacts manifests itself by the fact that the Fourier domain, i.e., a Fourier transformed space of the sampled volume, has one or more contiguous areas that are approximately zero and, therefore, are missing, but this is not associated with an object property. In such a case they are described as artifacts due to an incomplete sampling. In this case the class of these artifacts in the image domain or spatial domain generally also depends on their localization in the volume. When individual volumes are registered with respect to one another, the situation arises that corresponding image areas differ in the manifestation of their artifacts. Therefore, the use of a similarity measure is susceptible to errors, since the same object areas in the discrete sampling are similar only up to a certain and possibly insufficient degree. As a consequence, the registration contains errors that are reflected in the accuracy of the determined coordinate transformation. Thus, significant artifacts are to be expected after the individual volumes have been merged.

In the case of known cone beam computed tomography scanners, an X-ray image recording unit consisting of an X-ray emitter and a detector, preferably a flat detector, rotates around a scan center while at the same time recording a series of X-ray projection views in a scan plane. Such cone beam computed tomography scanners can be designed as gantry-based systems with the option of continuous rotation, but, in particular, also include stationary or mobile C-arms, as well as additional systems for position detection in radiation therapy or also micro computed tomography scanners in preclinical research or in materials science. An X-ray volume can be reconstructed from the recorded X-ray projections of a scan. If the region of interest (ROI) in an object is small compared to the reconstructed volume, then the diagnostic information about the volume is obtained with a single scan. However, a first volume, which is reconstructed from a single scan to generate a 3D data set, is too small for certain diagnostic tasks. In order to enlarge a reconstructed volume, a 3D data set is generated by means of at least one additional scan, the reconstruction of which results in a second volume that differs from the first volume, with the edge regions of the first and second volumes overlapping. Such a procedure can be expanded by adding additional volumes to the last reconstructed volume in order to generate even larger volumes. If the ROI is large compared to a reconstructed volume, then it is known to record the projection data of the entire ROI by taking additional scans with offset scan planes and to reconstruct a composite volume.

Some examples of its application are the generation of the volume of an entire spine or the tracking of a bolus over the length of an entire leg or the acquisition of the volume of a whole body. If the object or the support structure thereof and the cone beam computed tomography scanner are referenced with respect to one another, then the coordinate transformation between the two scan planes is known when the scan plane is shifted for the purpose of recording another X-ray projection data set. This is usually the case with stationary CT devices.

However, when a mobile cone beam computed tomography scanner, such as, for example, a mobile C-arm is used, a referencing within a calibration run is necessary after the C-arm has been positioned with respect to the object on a support structure, with the result that the referencing loses its validity if the C-arm is moved in a manner that cannot be reproduced.

If a coordinate transformation between the coordinate system of the cone beam computed tomography scanner and the coordinate system of the object and, if the object is positioned during the X-ray examination in a fixed spatial relationship to the support structure, for example, a patient couch, to the coordinate system of the support structure is not known, then a coordinate transformation can be determined in the above manner in such a way that the absorption values of the voxels in the corresponding overlapping areas match as closely as possible.

It is known that cone beam computed tomography scanners generate so-called cone beam artifacts based on an incompletely sampled Fourier domain. As a result, the greater the distance of a volume area from the central layer or, more specifically, the central scan plane, the more severe these artifacts are. In this case a structure, similar to a double cone with an opening angle, remains in the Fourier domain, within which no measured values, in particular, no frequencies, are recorded. Furthermore, it is also known that a computed tomography scanner, which cannot be completely traversed, for example, due to impending collisions with the support structure, does not scan certain areas in the Fourier domain due to the lack of angular coverage. The known algorithms for registering image volumes do not take into account the presence of such artifacts, for which reason their use leads to registration errors; and the composite volume, composed of partial volumes, has visible transitions between the two individual volumes.

The methods of the present technology can utilize the provision of two overlapping volumes and an estimated coordinate transformation between the position of the two volumes.

Moreover, in some embodiments, the overlapping area of the first and the second volume should be as small as possible in order to keep, for example, the radiation dose, administered to the patient, as low as possible or to keep the time required to record the total volume as short as possible; on the other hand, the overlap may not be too small in order to be able to calculate the relative position and orientation of the first volume to the second volume during the registration, with the objective of being able to merge the individual volumes with as few artifacts as possible.

If the volumes of the object under examination and the image recording device are not registered with respect to one another, overlapping individual volumes, which are recorded one after the other in the described and well-known manner, can be registered with respect to one another after the recording and then combined by means of a software algorithm to form a composite volume, which, however, may have the errors mentioned in the form of visible artifacts.

Figure 1:
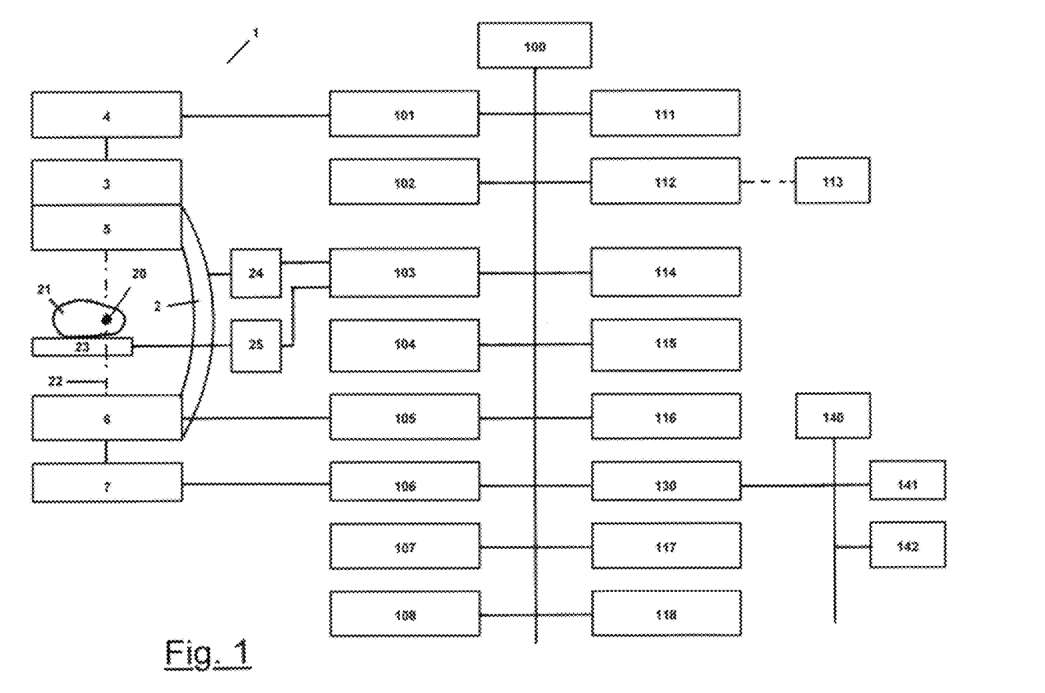
FIG. 1 illustrates a schematic representation of a cone beam computed tomography scanner, using the example of a C-arm.

FIG. 1 shows in schematic form a C-arm X-ray system 1, which is provided for the implementation of the method for recording the projection views of a scan.

A C-arm 2 carries the X-ray tube 3, the collimator 5 and at least parts of the high voltage generator 4 at one end; and at its other end and opposite the X-ray tube 3 said C-arm carries an X-ray image detector 6, in particular, a flat panel detector FPD. The C-arm 2 can be adjusted in a motor-controlled manner in several axes in space, the axes having sensors for detecting the degree of the adjustment. In particular, the C-arm 2 is held in a holder in such a way that said C-arm can be moved by a motor along its circumference. This movement is called the orbital movement/orbital axis. The C-arm holder (not shown) can be moved by a motor in at least one horizontal and one vertical axis. A C-arm X-ray system 1, which is equipped with these three motorized axes, is configured to implement a scan, with a scan plane 51, with a series of 2D X-ray projection recordings for a subsequent reconstruction of an X-ray volume with plane trajectories of the focal point 8 about a scan center 20.

An X-ray tube 3 generates an X-ray focus and is designed preferably as a rotating anode X-ray tube.

An oil-filled high voltage generator 4 provides all of the parameters required to operate the X-ray tube 3, such as acceleration voltage, tube current, cathode heating current, rotating anode motor current, pulse frequency and pulse width.

A controllable collimator 5 is provided preferably between the X-ray focus and the object 21, in order to collimate the X-ray beam emerging from the focus. It is provided that the aperture is changed as a function of the scan angle.

An X-ray image detector 6, in particular, a flat panel detector [FPD], is arranged on the circular arc shaped C-arm 2 at a specific distance and in a specific orientation to the focus and to the C-arm 2. It is provided to design the distance and the orientation of the X-ray image detector 6 in such a way that said distance and orientation can be reproduced and changed in a controlled manner.

During the recording of a projection, a projection image generation unit 7 generates a raw image of a projection of the object from the read image data of the X-ray image detector 6; and said raw image is fed to an image processing and storage unit 106.

A scan center 20 represents the center of the region of interest (ROI) 50, which is to be reconstructed, inside the object 21.

The connecting line between the X-ray focus and the center of the input window of the X-ray image detector 6 or another X-ray receiver is referred to as the central beam 22. It lies in the orbital plane of the C-arm perpendicular to the input window of the X-ray image detector 6.

An object 21 to be examined is placed on a support structure 23, preferably a patient couch. The support structure 23 can be designed in such a way that after an initial alignment with respect to the C-arm X-ray system 1 said support structure remains rigid while the object 21 is being scanned. Furthermore, it is also provided to equip the support structure 23 with motor-controlled, adjustable axes and to control the movement of the support structure 23 by means of a support structure motor control unit 25 synchronously with the movement of the C-arm X-ray system 1, or to set a specific position and orientation of the support structure 23. It is provided to program the movement control unit 103 for recording a series of scans, in order to generate a composite volume, in such a way that the object 21 is initially positioned with respect to the C-arm X-ray system 1 in such a way that the scan center and the scan plane are positioned in accordance with the given examination task, for example, in the center of a first ROI. In this orientation a scan is recorded, for example, with a series of X-ray projection recordings; and from the projection data set a volume is reconstructed, the coordinate system of which corresponds to that of the C-arm X-ray system 1. For the next scan of a series of scans, the object 21 is now moved, for example, along the scan axis, which runs through the first scan center and is perpendicular to the first scan plane, by a distance that corresponds, for example, to three quarters of the extent of the ROI in the direction of the scan axis. The C-arm X-ray system 1 remains spatially unchanged with its scan center and its orientation. Due to the sensors at the adjustment axes of the support structure 23 the position and the orientation of the object 21 can be approached by the movement control unit 103 in a manner that is reproducible. In the second scan position, another data set is now recorded in the spatially fixed coordinate system of the C-arm X-ray system 1; and the volume is reconstructed. In the event that the C-arm X-ray system 1 and the support structure 23 are referenced with respect to one another, the measured values of the displacement of the support structure 23 between the first and the second scan can be used to determine the instructions for the displacement of the second volume V2 in the coordinate system of the stationary C-arm X-ray system 1 in the form of a coordinate transformation T. By applying the coordinate transformation to the second volume V2, said second volume is shifted and rotated and, if necessary, deformed in such a way that corresponding object areas in the two overlapping areas of the two volumes (V1, V2) are represented by the same voxels. The voxels of the overlapping areas are then combined and averaged in a manner known from the prior art, in order to achieve a smooth transition between the two volumes.

In the event that the C-arm X-ray system 1 and the support structure 23 are not referenced with respect to one another, the two volumes can be moved and/or tilted relative to one another when the coordinate transformation is used, so that matching object areas come to lie in different voxel positions in the overlapping areas.

In order to orient the two volumes (V1, V2) in the correct position relative to one another, an optimal match of the corresponding object areas in the overlapping areas can be calculated in the manner described. The coordinate transformation determined in this way is now applied to the second volume; and the volumes, which are then oriented in the correct position, are then connected to one another in a manner that is well-known and for which the terms "sewn" or "stitched" are also used synonymously For a displacement of the scan plane and the scan center by means of the motorized movement of the support structure 23, communication between the C-arm X-ray system 1 and the support structure 23 is established by the movement control unit 103. Prior to the start of the first scan, the C-arm X-ray system 1 and the support structure 23 are brought into predetermined starting positions.

When the support structure 23 is ready for the recording of a first projection data set, the C-arm X-ray system 1 is precisely aligned. Thereafter, collision tests are optionally carried out, if necessary, for each position of the support structure 23 to be approached. In order to accelerate this process, in particular, when using a C-arm X-ray system 1, the collision tests can be conducted in both directions, for example, in the forward direction for a first individual volume and in the backward direction for a second volume.

In the event that the said X-ray system is applied to a patient, it may be necessary for the patient to stop breathing before the recording of a scan is started, in order to avoid the occurrence of movement artifacts. Then the recording protocol for all individual volumes should be carried out preferably without interruption. Therefore, a first scan is recorded; then the support structure 23 is moved; and then the recording of the second scan is started.

In the event that neither the C-arm X-ray system 1 nor the support structure 23 can be adjusted by means of a motor, but have position sensors in the adjustment axes, an operator interface/GUI/MMI is provided, through which the user is prompted to carry out the mechanical adjustment steps in each case, during which the correct execution is monitored (for example, whether the support structure 23 is in the correct position taking into account a predetermined tolerance). In the additional absence of an interface, there is no need to check the correct execution by means of the C-arm X-ray system 1.

In the presence of a motorization, but in the absence of a position sensor, the C-arm X-ray system 1 can be calibrated with respect to the motor(s) of the patient couch.

In order to carry out the measure of similarity, the C-arm X-ray system 1 has a volume comparison unit 102, in which the frequency representations of the two volumes, said representations having been generated in a Fourier transformation and filtering unit 118, are compared with the objective of determining the optimal registration information or, more specifically, an optimal coordinate transformation between the two volumes.

The volume comparison unit 102 is configured to receive a first volume of a part of an object with a spatially fixed first coordinate system and a second volume of another part of the object, which overlaps with the first part of the object, with a second coordinate system and an estimated coordinate transformation between the first and the second coordinate system, with the second coordinate system being transformed approximately into the first coordinate system K1 by means of the estimated coordinate transformation T12. In the X-ray system of the present technology the two volumes represent the filtered X-ray volumes of the overlapping volumes determined on the basis of the estimated coordinate transformation. For this purpose, the reconstructed X-ray volumes are made available to the Fourier transformation and filtering unit 118, which in each case performs a Fourier transformation and a filtering of the data in the frequency domain. The Fourier-transformed and optionally filtered data are called Fourier volumes in the following.

The optimal coordinate transformation that is determined in the iteration process is outputted by the volume comparison unit 102. The outputted coordinate transformation T12 is received by the reconstruction unit 117, in order to move the second individual volume V2 relative to the volume V1 in such a way that the result is a combination volume that consists of the first volume V1 and the second volume V2, and wherein the two volumes are combined with one another in the correct position.

A C-arm X-ray system motor control unit 24 controls all of the motor-adjustable axes of the C-arm X-ray system 1 and provides the movement control unit 103 with measured values from the position sensors of non-motor-adjustable axes.

A support structure motor control unit 25 and a C-arm X-ray system motor control unit 24 are driven synchronously by the movement control unit 103 of the C-arm X-ray system 1.

A higher level system control unit 100 has preferably a bus system with a large number of control, computing, and memory components.

An X-ray emitter control unit 101 controls the high voltage generator 4, the X-ray tube 3 and the collimator 5. Said X-ray emitter control unit has a dose rate control or automatic exposure control AEC, which controls the parameters of the X-ray tube 3 during an X-ray image recording in such a way that the X-ray detector 6 generates an X-ray image with a predetermined quality, for example, with a predetermined signal/noise ratio.

The C-arm X-ray system 1 has a movement control unit 103, which receives the focus trajectory, determined in the scan parameter generating apparatus 107, and the position of the scan center with respect to the focus trajectory, in particular, in the case of a design as a C-arm.

An image recording control unit 104 triggers the recording of a projection view unless a prevention signal prevents the triggering of the recording. Especially in the case of a C-arm, a prevention signal is generated, for example, by a collision, which was recognized immediately beforehand, or by an emergency stop of the X-ray system that was triggered by an operator. Upon triggering the recording of a projection, the control of the tube current, the tube voltage and/or the exposure time in an exposure control of the X-ray emitter control unit 101 is used to administer a dose that produces a projection recording of a selected quality in the X-ray detector 6. For example, the signal-to-noise ratio can be specified as a measure of the image quality.

An X-ray detector control unit 105 controls and monitors all of the functions of the X-ray detector 6, such as, for example, the image recording, the image reading, the dark current as well as the gain correction and the removal of residual charges after the end of the exposure time.

In an image processing and storage unit 106, the raw image data from the projection image generation unit 7 are corrected, filtered or processed and stored in accordance with predetermined image processing algorithms. Then they are available to the reconstruction unit 117 for carrying out the reconstruction of a volume.

All of the parameters for a scan are generated in a scan parameter generation unit 107. In this case the scan parameter generation unit 107 receives, for example, the position of the scan center 20 in the coordinate system of the C-arm X-ray system 1, a focus and a detector trajectory, a total number of the planned X-ray projection recordings of the scan and a provided tube voltage for the scan. The generated scan parameters are made available in the movement control unit 103, the X-ray emitter control unit 101 and the image recording control unit 104 and other units, for example, a Fourier transformation and filtering unit 118.

The scan parameter generation unit 107 is configured to receive the position of a scan center 20 in the coordinate system of the C-arm X-ray system 1. The scan center can be determined, for example, by manually aligning the central beam 22 with respect to the scan center 20 in two mutually independent spatial directions and can be entered into the system control unit by an operator.

The scan parameter generation unit 107 is further configured to receive trajectories of the focus 8 and the X-ray detector 6 in the coordinate system of the C-arm X-ray system 1. In particular, when using a C-arm X-ray system 1, the trajectories are received by an organ program database 115, after they have been selected by an operator and, if necessary, adapted to the given examination situation, for example, to the patient's dimensions.

At least one display 111 is provided for the output of the image data, the control data and the patient data. Instructions for an operator 113 are entered into the system control unit 100 by means of an input unit 112. It is provided that at least one display 111 is designed as a graphical user interface GUI.

An input device unit 112 is used to enter operating commands from the operator 113 and to import system programs into the system, provided they cannot be imported over a network 140.

The system controller 100 has a mass storage device 116 and an output unit 114. An output unit 114 is defined as any device, by means of which examination results and/or system parameters can be outputted on any type of information carrier.

The system controller 100 has an organ program database 115, in which the X-ray and scan parameters for various diagnostic tasks are stored in such a way that they can be retrieved. In this case the individual organ programs can be adapted by an operator 113 to the existing circumstances, for example, the patient's dimensions and to the current diagnostic task. An organ program can represent, for example, the recording of a spine or leg from the groin to the foot.

The system control unit 100 has a reconstruction unit 117, in which the processed and stored projection data from the image processing and storage unit 106 are received together with the corrected data for the projection geometries of the respective projection recordings from the movement control unit 103; and a 3D volume is reconstructed.

The system control unit 100 has preferably a DICOM interface 130 to a network 140, by means of which the inputs and the outputs between the C-arm X-ray system 1 and, for example, a hospital information system HIS 142, a radiology information system RIS 141 and a global network are accomplished. The DICOM input is provided to transfer patient data and patient-specific scan parameters from previous examinations.

If a cone beam computed tomography scanner, in particular, a C-arm X-ray system 1, has, in addition to the three controllable adjustment axes described above, another with an adjustment component perpendicular to the orbital plane, then it is possible to implement non-planar focus trajectories.

The relationship between the position values of the drive motors and the pair of points on the detector and the focus trajectories can be calculated in theory from knowledge of the kinematics of the C-arm 2, but is checked in the usual manner by means of a calibration run. Deviations from the theoretical kinematics are corrected in the course of a calibration run and are stored as the calibrated kinematics preferably in LUTs in a memory of the C-arm X-ray diagnostic system in such a way that they can be retrieved and are taken into account during volume reconstruction. Therefore, for reconstruction of a volume, the projection geometries of the calibrated kinematics are used for each projection recording.

Figure 2:
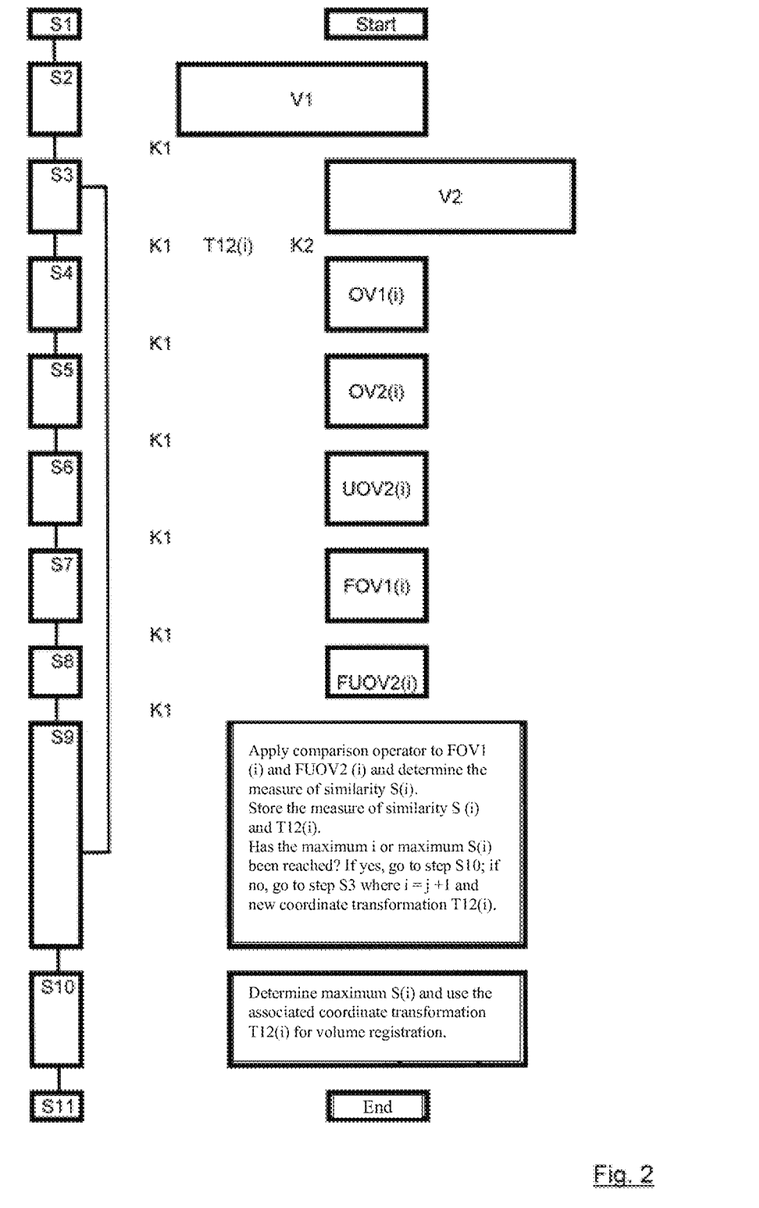
FIG. 2 illustrates a schematic representation of method steps performed by an X-ray system.

FIG. 2 shows in schematic form the method steps of the X-ray system of the present technology for iteratively determining optimal registration information between two overlapping volumes.

First, a first spatial domain of a composite volume is discretely sampled with a measuring device, for example, a C-arm X-ray system 1, and a first volume V1 is reconstructed from the volume data set obtained in this way. Then the measuring device is moved relative to the composite volume; and a second spatial domain, overlapping with the first spatial domain, is discretely sampled; and a second volume V2 is reconstructed from the volume data set obtained in this way. The volume V1 is shown in a coordinate system K1; and the volume V2 is shown in a coordinate system K2. The coordinate system K2 is transformed into the coordinate system K1 by means of a coordinate transformation T12 to be determined. As an alternative, the coordinate system K1 is transformed into the coordinate system K2 by means of the inverse coordinate transformation T21. In order to accelerate the convergence of the iteration when determining the optimal coordinate transformation T12 or T21, an estimated coordinate transformation is given. The estimate can be obtained based on the approximate knowledge of the displacement of the measuring apparatus; it is also provided in the context of the present technology to obtain an estimate of the coordinate transformation from a first evaluation of any high contrast landmarks in the two volumes V1 and V2.

In step S2 of the method the first volume V1 with the coordinate system K1 is received; and in step S3 of the method the second volume V2 with the coordinate system K2 and an initial estimated coordinate transformation T12 is received. The initial coordinate transformation is used as the start value T12 for the first iteration step.

The reconstruction of the individual volumes V1 and V2 is carried out preferably immediately after the respective volume data set has been recorded. If more than two individual volumes are to be combined to form a composite volume, then the recording of further volume data sets and the reconstruction of additional partial volumes can have already taken place during the iteration process.

If a composite volume is to be composed of three or more partial volumes, then a first composite volume is formed initially from two partial volumes, and the third partial volume is added to said first composite volume. In this case the first composite volume in the iteration is treated in the same way as the first volume V1; and the third partial volume is treated in the same way as the second volume V2. It can be advantageous if a partial volume in the interior of the composite volume is selected as the first volume V1; and the addition of other partial volumes takes place successively in two spatial directions. As a general principle, when using a parallel computer, the coordinate transformations between the first volume V1 and the additional partial volumes, adjacent to said first volume, can be determined in parallel.

In step S4 of the method the overlapping volume OV1 (*i*) of the first volume V1 is determined in the iteration step i, under the assumption of the coordinate transformation T12 (*i*) in the coordinate system K1.

In step S5 of the method the overlapping volume OV2 (*i*) of the second volume V2 is determined, under the assumption of the coordinate transformation T12 (*i*) in the coordinate system K1.

In general, the calculated overlapping volumes OV1 (*i*) and OV2 (*i*) have a different grid structure of the voxels. The voxel grids of the overlapping volumes can be moved with respect to one another by fractions of the grid period; and the grid axes can be tilted relative to one another. In step S6 of the method the voxels of the overlapping volume OV2 (*i*) are converted to voxels in the grid of the voxels of the overlapping volume OV1 (*i*) by means of well-known methods, such as interpolation, between the next neighboring voxels or by volume resampling. The grid points of the voxels of the converted overlapping volume UOV2 (*i*) lie on the grid points of the voxels of the overlapping volume OV1 (*i*) in the coordinate system K1. As a result, each grid point in the area of the overlapping volumes has a voxel value from the first volume V1 and a converted voxel value from the second volume V2.

In step S7 of the method a bandpass filter is applied to the overlapping volume OV1 (*i*); and in step S8 of the method a bandpass filter is applied to the overlapping volume UOV2 (*i*). A bandpass filter is applied to the overlapping volume OV1 (*i*) and to the converted overlapping volume UOV2 (*i*), in each case in the manner described above; and said bypass filter adjusts temporarily or reversibly the Fourier domains of the two overlapping volumes in such a way that both contain only those frequencies that are also included in the respective other.

It is provided that the bandpass filter applies a spectral analysis to the Fourier representations of the two overlapping volumes and filters the Fourier domains in such a way that all of the frequencies are removed from the Fourier spectrum that are not present in the Fourier spectrum of the other overlapping volume. In this way two filtered Fourier domains of the overlapping volumes are obtained. They in turn are transformed back into the spatial domain; and corrected voxel values of the volumes FOV1 (*i*) and FOV2K1 (*i*) are obtained in the coordinate system K1. In these volumes the artifacts are partially intensified as compared to the overlapping volumes OV1 (*i*) and UOV2 (*i*), because they match in their appearance.

As an alternative, it is provided that the bandpass filter acts directly in the spatial domain, but its effect adjusts the two Fourier domains in the same way, without explicitly carrying out a Fourier transformation. Here, too, corrected voxel values of the volumes FOV1 (*i*) and FOV2K1 (*i*) are obtained in the coordinate system K1. In these volumes, the artifacts are again partially intensified as compared to the overlapping volumes OV1 (*i*) and UOV2 (*i*), because they match in their appearance.

In step S9 of the method a measure of similarity is applied to the filtered overlapping volumes FOV1 (*i*) and FUOV2 (*i*). The measure of similarity S (i) and the associated coordinate transformation T12 (*i*) are stored in a memory. If a maximum number of iteration steps has been reached or if a maximum value of the measure of similarity S (i) has been reached, at which no improvement in the measure of similarity S (i) could be expected for further iterations, then the iteration is terminated; and a jump is made to step S10 of the method. If this is not the case, then a jump is made to step S3, while increasing the value of i to i+1 and a new coordinate transformation T12 (*i*+1). In this case this new coordinate transformation is determined as efficiently as possible by the optimization method that is used. In this case it is also provided that an optimization method, for example, a method from the family of genetic optimization, checks, for example, execution in parallel, more than one coordinate transformation T12 (*i, j*) for each iteration step i and uses this to create a new set of coordinate transformations T12 (*i*+1, j) that is used in the next iteration step i+1.

The automatic determination of the selection of the coordinate transformations T12 (*i*) is, for example, but not exclusively, limited to the examples below; an optimization algorithm from the set of the following algorithms is provided:
methods from convex or non-convex optimization, such as gradient descent, (L−) BFGS (−B), Nelder-Mead, genetic optimization, simulated annealing,
methods from the field of phase correlation, in order to be able to work directly in the Fourier domain.

Such an optimization algorithm is designed to automatically select the coordinate transformations, so that the measure of similarity gradually approaches the optimal value.

In step S10 of the method the optimal measure of similarity S (i) is determined; and the associated coordinate transformation T12 (*i*) is made available as the optimal registration information for further use.

The optimal coordinate transformation T12 (*i*) from step S10 of the method is used to combine the first volume V1 with the second volume V2 in accordance with a method known from the prior art. For this purpose the entire volume V2 is transformed into the coordinate system K1; and then the voxel values of the entire volume V2 are converted to voxels in the grid of the voxels of the first volume V1 by means of well-known methods, such as interpolation between the next neighboring voxels or by volume resampling. The grid points of the voxels of the converted overlapping volume UV2 lie on the grid points of the voxels of the volume V1 in the coordinate system K1. As a result, each grid point has in the area of the overlapping volumes a voxel value from the first volume V1 and a converted voxel value from the second converted volume UV2.

Figure 3A:
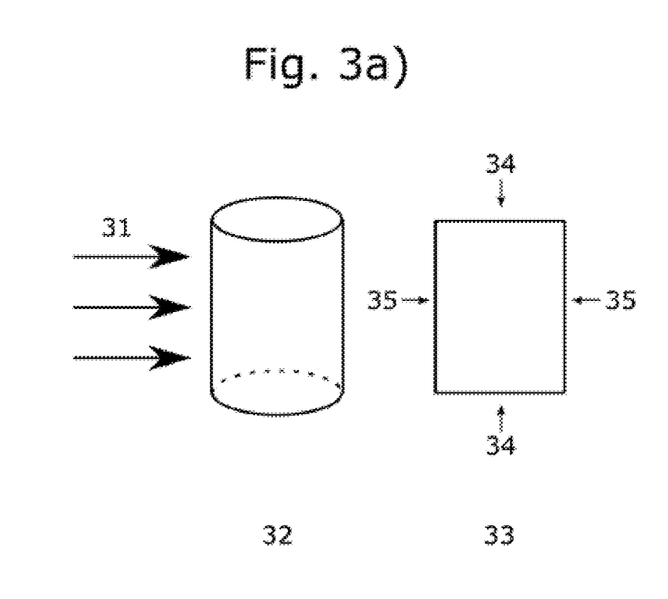
FIG. 3a illustrates a schematic representation of a projection of an object by means of a parallel beam geometry.
Figure 3B:
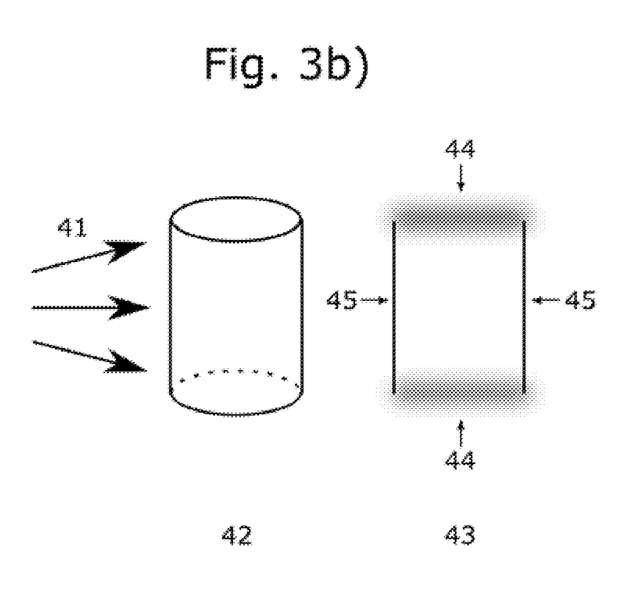
FIG. 3b illustrates a schematic representation of a projection of an object by means of a cone beam geometry.

FIG. 3a and FIG. 3b show in schematic form projections on the basis of the radiation source geometries that have been selected in different ways.

FIG. 3a shows a parallel beam geometry 31. Then the parallel beams 31 depict a three dimensional object 32 as a two dimensional structure 33. When a parallel beam geometry 31 is used, the three dimensional object 32 is depicted in such a way that all edges 34 and 35 of the two dimensional structure 33 can be displayed completely and sharply.

FIG. 3b shows a cone beam geometry 41. Then the cone beams 41 depict a three dimensional object 42 as a two dimensional structure 43. When cone beams 41 are used, the three dimensional object 42 is depicted in such a way that not all of the edges of the two dimensional structure 43 are shown in sharp detail. The edges, which are completely scanned by the cone beams, are depicted as sharp edges 45. The edges, which are not completely (incompletely) scanned by the cone beams, are depicted as fuzzy edges 44. These structures, which are depicted as fuzzy edges 44, correspond to an incompletely sampled space.

LIST OF REFERENCE NUMERALS AND SYMBOLS

1 C-arm X-ray system
2 circular arc shaped C-arm
3 X-ray tube
4 high voltage generator
5 collimator
6 X-ray image detector
7 projection image generation unit
20, 20', 20" scan center
21 object
22 central beam
23 patient couch
24 cone beam computed tomography scanner motor control unit
25 support structure motor control unit
50 ROI
51, 51', 51" scan plane
100 system control unit
101 X-ray emitter control unit
102 volume comparison unit
103 movement control unit
104 image recording control unit
105 X-ray detector control unit
106 image processing and storage unit
107 scan parameter generation unit
108 overlapping volume determination unit
111 display
112 input device unit
113 operator
114 output unit
115 organ program database
116 mass storage
117 reconstruction unit
118 Fourier transformation and filtering unit
130 DICOM interface
140 network
141 RIS radiology information system
142 HIS hospital information system
31 parallel beam geometry
32 three dimensional object
33 two dimensional structure
34 completely depicted edge
35 completely depicted edge
41 cone beam geometry 42 three dimensional object
43 two dimensional structure
44 completely depicted edge
45 incompletely depicted edge
V1 first volume
V2 second volume
K1 coordinate system of the first volume
K2 coordinate system of the second volume
T12 (i) coordinate transformation of the ith iteration step between the coordinate system
K1 and the coordinate system K2
OV1 (i) overlapping volume of the first volume V1 in the coordinate system K1 for the iteration step i
OV2 (i) overlapping volume of the second volume V2 in the coordinate system K1 for the iteration step i
UOV2 (i) converted overlapping volume in the coordinate system K1, in which the voxels of the overlapping area OV2 (i) are converted to voxels in the grid of the overlapping area OV1 (i).
UV2 converted second volume in the coordinate system K1, in which the voxels of the second volume V2, which are transformed with the optimal coordinate transformation T12, in the coordinate system K1 are converted to voxels in the grid of the voxels of the first volume V1.
F bandpass filter
FOV1 (i) overlapping volume with changed voxel values after application of the bandpass filter F to the volume OV1 (i)
FUOV2 (i) overlapping volume with changed voxel values after application of the bandpass filter F to the volume UOV2 (i)
S (i) measure of similarity of the ith iteration step Other, particularly advantageous embodiments and further developments of the present technology shall become apparent from the dependent claims and the description, where in this case the independent claims of one category of claims can also be further developed analogously to the dependent claims of another category of claims; and, in particular, individual features of different exemplary embodiments or variants can be combined to form new exemplary embodiments or variants.

What is claimed is:

1. An X-ray system suitable for iterative determination of an optimal coordinate transformation between a first N-dimensional partial volume V1 and a second N-dimensional partial volume V2 of an extended object, wherein the partial volume V1 and the partial volume V2 partially overlap in overlapping volumes OV1 and UOV2, said X-ray system comprising an imaging device and one or more processors configured to perform operations comprising at least:
    a) recording, using the imaging device, the partial volume V1 and the partial volume V2 by discrete sampling of the extended object;
    b) applying a bandpass filter to the overlapping volumes OV1 and UOV2 within each of a plurality of iteration steps i to obtain filtered overlapping volumes FOV1 (i) and FOV2 (i), wherein applying said bandpass filter comprises:
        removing, from the overlapping volume OV1 (i), frequencies that are not contained in the overlapping volume UOV2 (i); and
        removing, from the overlapping volume UOV2 (i), frequencies that are not contained in the overlapping volume OV1 (i); and
    c) determining the optimal coordinate transformation by iterative optimization of a measure of similarity between the filtered overlapping volumes FOV1 (i) and FUOV2 (i).

2. The X-ray system as claimed in claim 1, wherein the bandpass filter determines the frequencies which are to be removed based on information about a scanning mode or a scanning geometry.

3. The X-ray system as claimed in claim 1, wherein the bandpass filter determines the frequencies to be removed in a Fourier domain of the overlapping volumes OV1 (i) and UOV2 (i) based on an absolute amount present therein falling below a predetermined threshold value.

4. The X-ray system as claimed in claim 1, wherein the frequencies to be removed are removed temporarily from the two overlapping volumes by the bandpass filter in a spatial domain and separately for each recording of the overlapping volumes OV1 (i) and UOV2 (i) before calculation of the measure of similarity.

5. The X-ray system as claimed in claim 1, wherein the frequencies to be removed are removed temporarily from a Fourier domain of the two overlapping volumes OV1 (i) and UOV2 (i) by the bandpass filter in the Fourier domain and separately for each iteration step i before calculation of the measure of similarity, under a current assumption of a coordinate transformation.

6. The X-ray system as claimed in claim 1, further comprising a cone beam computed tomography scanner configured to perform the recording of the partial volume V1 and the partial volume V2.

7. The X-ray system as claimed in claim 6, wherein the cone beam computed tomography scanner is a mobile C-arm.

8. The X-ray system as claimed in claim 6, wherein the overlap of the two partial volumes V1 and V2 is achieved by adjusting a support structure of the extended object, and wherein the cone beam computed tomography scanner is configured to prompt an operator to perform a manual adjustment of the support structure before the start of the recording and to receive a confirmation of the manual adjustment from the operator.

9. The X-ray system as claimed in claim 8, wherein the support structure has a position sensor, and wherein the cone beam computed tomography scanner ensures a correct adjustment by monitoring the position sensor.

10. The X-ray system as claimed in claim 6, wherein the cone beam computed tomography scanner is moved in space with respect to the extended object to achieve the overlap.

11. The X-ray system as claimed in claim 10, wherein the cone beam computed tomography scanner is moved by a motor.

12. The X-ray system as claimed in claim 10, wherein the cone beam computed tomography scanner has a position sensor and ensures a correct overlap of the partial volumes V1 and V2 by evaluating the position sensor.

13. The X-ray system as claimed in claim 6, wherein the overlap of the two partial volumes V1 and V2 is achieved by adjusting a support structure of the extended object, and wherein a determined coordinate transformation between the cone beam computed tomography scanner and the object support structure is stored.

14. The X-ray system as claimed in claim 13, wherein the stored coordinate transformation is used to combine subsequently recorded partial volumes, directly without re-optimization.

15. The X-ray system as claimed in claim 1, wherein the overlap of the two partial volumes V1 and V2 is achieved by adjusting a support structure of the extended object.

16. The X-ray system as claimed in claim 15, wherein the support structure is adjustable by a motor.

17. The X-ray system as claimed in claim 16, further comprising a cone beam computed tomography scanner configured to perform the recording of the partial volume V1 and the partial volume V2, wherein the motor adjusts the support structure by means of the cone beam computed tomography scanner to achieve the overlap.

18. The X-ray system as claimed in claim 1, wherein the X-ray system is further configured to combine the partial volumes V1 and V2 into a combined volume using the determined optimal coordinate transformation.

19. The X-ray system as claimed in claim 18, wherein the combining the partial volumes V1 and V2 comprises, after applying the coordinate transformation at each coordinate, generating the combined volume in the overlapping area of the partial volumes V1 and V2 by weighted averaging of the measured values present in the partial volumes V1 and V2 at each coordinate.

20. The X-ray system as claimed in claim 19, wherein a weight of the weighted averaging is a function of a cone beam angle present at a coordinate.

21. The X-ray system as claimed in claim 18, wherein the combined volume is generated in the overlapping area of the partial volumes in such a way that the frequencies contained in a Fourier domain of one of the overlapping volumes are first transmitted to a Fourier domain of the other overlapping volume at such points where the other overlapping volume has no frequencies.

22. The X-ray system as claimed in claim 1, wherein, after the combination of the partial volumes V1 and V2, further partial volumes are added to the resulting combined volume.

23. A tangible, non-transitory computer-readable storage medium having stored thereon a computer program which can be loaded directly into a storage unit of a control unit of a cone beam computed tomography scanner, in particular, a C-arm, with program sections that causes an X-ray system comprising the cone beam computed tomography scanner to carry out steps a-c of claim 1 when the computer program is executed in the control unit of the cone beam computed tomography scanner.

24. A tangible, non-transitory computer-readable storage medium having stored thereon program sections which, when read and executed by a computer unit, cause an X-ray system comprising the computer unit to carry out steps a-c of claim 1.

* * * * *